United States Patent [19]

Nordfang et al.

[11] Patent Number: 5,219,993

[45] Date of Patent: Jun. 15, 1993

[54] METHOD OF RECOVERING PURIFIED EPI PROTEIN FROM A SOLUTION ESPECIALLY A FERMENTATION SOLUTION

[75] Inventors: Ole Nordfang, Hilleroed; Soren Carlsen, Birkeroed, both of Denmark

[73] Assignee: Novo Nordisk A/S, Bagsvaerd, Denmark

[21] Appl. No.: 730,860

[22] PCT Filed: Jan. 18, 1990

[86] PCT No.: PCT/DK90/00016

§ 371 Date: Aug. 12, 1991

§ 102(e) Date: Aug. 12, 1991

[87] PCT Pub. No.: WO90/08158

PCT Pub. Date: Jul. 26, 1990

[30] Foreign Application Priority Data

Jan. 19, 1989 [DK] Denmark ............... 4123/89

[51] Int. Cl.$^5$ .................. C07K 3/20; A61K 35/16
[52] U.S. Cl. .................... 530/380; 530/413; 530/417
[58] Field of Search .......... 530/380, 413, 417

[56] References Cited

U.S. PATENT DOCUMENTS 4,721,572 1/1988 Jordan ................... 210/635

OTHER PUBLICATIONS

Shing et al. Heparin Affinity: Purification of a Tumor-Derived Capillary Endothelial Cell Growth Factor, Science vol. 223, pp. 1296–1298, 1984.
Broze and Miletich, Isolation of Tissue Factor Inhibitor Produced by HepG$_2$ hepatoma cells. PNAS vol. 84, pp. 1886–1890, 1987.
Cramer et al., Thrombosis Research, vol. 48, pp. 11–22 (1987).
Sandset et al., Thrombosis Research, vol. 47, pp. 389–400 (1987).

Primary Examiner—Jeffrey E. Russel
Assistant Examiner—P. Lynn Touzeau
Attorney, Agent, or Firm—Steve T. Zelson

[57] ABSTRACT

The EPI protein is isolated and purified from a fermentation solution, using chromatographic technique, wherein the solution containing the EPI protein is applied to a matrix coupled with heparin, preferably heparin-Sepharose.

3 Claims, No Drawings

METHOD OF RECOVERING PURIFIED EPI PROTEIN FROM A SOLUTION ESPECIALLY A FERMENTATION SOLUTION

The present invention refers to a method of isolating and purifying the EPI protein.

BACKGROUND OF THE INVENTION

Blood coagulation is a complex process involving many activating and inactivating coagulation factors. Anticoagulant proteins are known to be important for regulation of the coagulation process. See B. Lammle and J. Griffin (Clinics in Haemotolog 14, p. 281-342, 1985) for a review on coagulation inhibitors and regulation of coagulation.

Thus heparin is used clinically to increase the activity of antithrombin III and heparin cofactor II. Antithrombin III is used for the inhibition of factor Xa and thrombin. Hirudin is used for the inhibition of thrombin Protein C may be used for the inhibition of factors V and VIII.

Coagulation can be initiated through the extrinsic pathway by the release of tissue factor (J.H. Morrissey et al.: Thromb Res 50, p. 481-93, 1988). Coagulation activation by the extrinsic pathway may be inhibited by different mechanisms (P.M. Sandset et al.: Thromb Res 47, p. 389-400, 1987; B.J. Warn-Cramer et al.: Thromb Res 4s, p. 11-22, 1987; S. Kondo and W. Kisiel: Blood 70, p. 1947-54, 1987; S.D. Carson: J. Biol Chem 262, p. 718-21, 1987; G.J. Broze et al.: Blood 77, p. 335-43, 1988; S. Kondo et al.: Thromb Res 4s, p. 449-59, 1987).

The basic trigger in many coagulation disorders is the release of tissue factor and thus activation of factor X by factor VII-tissue factor. During surgery, tissue factor is released and thrombi may be formed In heart attack a primary thrombus is formed and when this thrombus is released, tissue factor is exposed and coagulation is initiated resulting in a secondary, perhaps lethal thrombus. During sepsis, bacterial endotoxin induces the systemic release of tissue factor. This may lead to disseminated intravascular coagulation (DIC). DIC can be treated with antithrombin III (T.E. Emerson et al.: Circulatory Shock 21, p. 1-13, 1987) Which inhibits the late steps in the coagulation cascade. Activated Protein C which inhibits in the middle of the coagulation cascade can also be used for the treatment of DIC (F.B. Taylor et al.: J Clin Invest 79, p. 918-25, 1987).

Protein showing extrinsic coagulation Pathway Inhibitor (EPI) activity has been recovered and isolated from human cells. It is known that EPI inhibits factor VII-tissue factor catalyzed activation of FX. However, the exact mechanism by which EPI inhibits coagulation is not known. Human plasma contains 3 molecular species showing EPI activity. The molecular masses are >500 kDa, 200 kDa and 40 kDa respectively (P.M. Sandset et al.: Thromb Res 47, p. 389-400, 1987).

The object of the present invention is an improved method to isolate the protein EPI in concentrated or pure form.

DETAILED DESCRIPTION OF THE INVENTION

Definitions: EPI is Extrinsic coagulation Pathway Inhibitor. EPI is a protein which shows activity in the assay described by Sandset et al. (Throm Res 47, p. 389-400, 1987). One unit of EPI is the amount of EPI activity found i 1 ml of normal human plasma.

The EPI protein may be recovered from supernatants of cell lines using precipitation and affinity chromatography on factor Xa. However, this purification procedure cannot be used in large scale owing to the very limited availability of factor Xa (G.J. Broze and J.P. Miletich, Proc Natl Acad Sci USA 84, p. 1886-1890, 1987).

It has now been found that a very efficient purification is obtained when the solution containing the EPI protein is applied to a matrix coupled with heparin.

The invention is based on the discovery that the EPI molecule contains a specific site having affinity to heparin. A column containing a matrix coupled with heparin will selectively bind the EPI protein.

A preferred matrix is heparin-Sepharose, from which the EPI protein may be eluted.

Thus it is possible to apply 100 vol. culture medium on 1 vol. heparin-Sepharose and 80% of the EPI activity will be found in the eluate.

On the other hand if an- or cation exchange is used the result will be poorer. 25 vol. of protein free culture medium applied on 1 vol. Q-fast flow Sepharose will only give 10% EPI activity in the eluate and 35 vol. of protein free culture medium applied on 1 vol. S-fast flow Sepharose will only give 1% EPI activity in the eluate.

It is also possible to use precipitation with $CdCl_2$ as a first step for purification of EPI but this will only give a specific activity of 8.5 U/mg (G.J. Broze and J.P. Miletich: Proc. Natl Acad Sci USA 84, p. 1886-1890, 1987). The invention is illustrated in the following with reference to the examples.

EXAMPLE 1

The human HeLa cell line was grown to confluency in Dulbecco-modified Eagles medium (DMEM) containing 10% fetal calf serum. The cell layer was washed free of serum proteins with serumfree DMEM and incubated in this medium at 37° C. in an atmosphere of 5% $C_2$. The medium was replaced and the spent medium frozen every two or three days.

Serum-free DMEM medium was harvested from the HeLa cell line as described above. 550 ml medium was applied over night at 4° C. on a column containing 4 ml heparin-Sepharose equilibrated with buffer A (20 mM tris, 10% glycerol, 0.1M NaCl, pH 7.5). The column was washed with 60 ml A and eluted with a gradient of 120 ml. A→B. Buffer B was 20 mM tris, 10% glycerol, 0.7M NaCl, pH 7.5. Fractions were collected and a pool was prepared from the fractions with highest activity The pool contained 153 units of EPI for each mg of protein. 4 ml of the heparin Eluate was further fractionated on a microbore ® RP4 column equilibrated in buffer C (0.1% TFA). EPI was eluted with a gradient from 25 to 60% of buffer D (60% isopropanol, 0.08% TFA) in buffer C. Elution was over 20 min with a flow of 0.15 ml/min. EPI eluted with a specific activity of 3600 units/mg protein (Table 1).

TABLE 1

Purification of EPI protein from serum-free HeLa culture medium

| Fraction | EPI activity U/ml | Volume ml | Yield from culture e med. | Spec. act. U/mg | Spec. act. rel. to human pl. |
|---|---|---|---|---|---|
| Culture medium | 0.56 | 550 | 100 | 5.6[a] | 400 |
| Heparin-Seph. el. | 5.4 | 35 | 61 | 153[b] | 10,900 |

TABLE 1-continued

Purification of EPI protein from serum-free HeLa culture medium

| Fraction | EPI activity U/ml | Volume ml | Yield from culture e med. | Spec. act. U/mg | Spec. act. rel. to human pl. |
| --- | --- | --- | --- | --- | --- |
| RP4 el. | 25.2 | 0.35 | 25 | 3600[b] | 260,000 |

[a]Serum-free culture medium contained 0.1 mg protein ml
[b]$E_{280}$ (1%) was set to 10.

EXAMPLE 2

Serum-free DMEM medium was harvested from the HeLa cell line as described in Example 1 600 ml medium was applied over night on a column containing 5.5 ml heparin-Sepharose equilibrated with buffer A (20 mM tris, 10% glycerol, 0.1M NaCl, pH 7.5). The column was washed with 20 ml buffer A and 80 ml buffer B (20 mM tris, 10% glycerol, 0.2M NaCl, pH 7.5). The column was eluted with buffer C (20 mM Tris, 10% glycerol, 0.7 M NaCl, pH 7.5). 12 ml eluate containing EPI was pooled. ml of the pool was diluted to 80 ml with buffer D (20 mM tris, 10% glycerol, pH 7.49. 75 ml was applied over 150 minutes on a mono-Q column equilibrated with buffer D. EPI was eluted with a gradient from 0 to 100% of buffer E (20 mM tris, 10% glycerol 0.5M NaCl, pH. 7.4). Elution was over 45 min with a flow of 0.5 ml/min. EPI eluted in 3 ml, with a specific activity of 1030 units/mg in the top fractions (Table 2).

TABLE 2

Purification of EPI proteins from serum-free HeLa culture medium.

| Fraction | EPI activity U/ml | Volume ml | Yield from culture med. | Spec. act. U/mg | Spc. act. rel. to human pl. |
| --- | --- | --- | --- | --- | --- |
| Culture med. | 0.46 | 600 | 100 | 4.6[a] | 326 |
| Heparin-Seph. eluate (step) | 18.0 | 12 | 78 | 58[b] | 4.100 |
| Mono Q eluate | 38.2 | 3 | 66 | 450[b] | 32,100 |
| MonoQ eluate top fraction | 49.5 | 1.5 | 43 | 1030[b] | 73,570 |

[a]Serum-free culture medium contained 0.1 mg protein/ml
[b]$E_{280}$ (1%) was set to 10

EXAMPLE 3

EPI from serum-free DMEM medium was purified using Heparin-Sepharose and Mono-Q as described in Example 2. 75 units of Mono-Q EPI eluate were fractionated on a microbore RP-4 column (Browmlee 2×30 mm). The column was equilibrated in 75% buffer A (0.1% TFA) and 25% buffer B (0.08% TFA, 60% isopropanol). EPI was in 120 minutes eluted with 24→60% buffer B at a flow rate of 0.15 ml/min. 54% of the applied EPI activity was recovered in the eluate. 17% of the applied activity was recovered in a fraction that only, apart from gel artefacts, contained one protein as detected from SDS-PAGE. The fraction contained 23.000 units of EPI activity for each mg of protein. The protein component was analyzed by measuring $E_{280}$ (E280, 1%=10) using applied Biosystems photometer. The molecular weight in reduced SDS-PAGE is estimated to be 43 kDa, N-terminal sequencing on an Applied Biosystems gasphase sequenator gave the following sequence: Asp Ser Glu Glu Asp Glu Glu His Thr Ile Ile Thr X X Glu Leu Pro, where the amino acids at X could not be identified.

EXAMPLE 4

EPI from serum-free DMEM medium was purified using Heparin-Sepharose and MonoQ as described in Example 3. 4 ml of Mono-Q eluate was diluted with 15 ml of buffer A (20 mM Na3-citrate, 10% glycerol, pH 5). The diluted sample was applied with a flow of 0.4 ml/min on a 1 ml Mono-S column equilibrated in buffer A. The column was washed with 10 ml of A and eluted in 50 minutes with a gradient of A→B (50 mM imidazol, 10% glycerol, 0.6M NaCl, pH 7.47). The flow was 0.5 ml/min. 58% of the applied amount of EPI was recovered with specific activity of 12.000 units/mg. The protein content was analyzed by measuring $E_{280}$ (E280, 1%=10) using a Pharmacia photometer.

EPI appears as a protein with a molecular weight of 43 kDa.

We claim:

1. A method for isolating and purifying an EPI protein from a cell line supernatant solution which method comprises:
    a) applying a cell line supernatant solution containing EPI protein to a chromatographic column containing a matrix coupled with heparin and
    b) applying a buffer solution to said chromatographic column to release and elute EPI protein bound to heparin in said chromatographic column matrix whereby isolated and purified EPI protein is eluted from said chromatographic column.

2. Method according to claim 1, wherein the chromatographic column matrix is heparin-Sepharose.

3. Method according to claim 2 or 1, wherein said supernatant solution is from the fermentation of a cell line.

* * * * *